(12) United States Patent
Tokuda

(10) Patent No.: US 6,979,828 B2
(45) Date of Patent: Dec. 27, 2005

(54) METHOD AND APPARATUS FOR IMMEDIATELY DETERMINING MICROORGANISM

(75) Inventor: Yoshiyuki Tokuda, Higashiyamato (JP)

(73) Assignee: Nippon Mizushori Giken Co. Ltd., Tokyo (JP)

(*) Notice: Subject to any disclaimer, the term of this patent is extended or adjusted under 35 U.S.C. 154(b) by 186 days.

(21) Appl. No.: 10/257,731

(22) PCT Filed: Feb. 15, 2001

(86) PCT No.: PCT/JP01/01089

§ 371 (c)(1),
(2), (4) Date: Apr. 21, 2003

(87) PCT Pub. No.: WO02/064818

PCT Pub. Date: Aug. 22, 2002

(65) Prior Publication Data

US 2003/0155528 A1 Aug. 21, 2003

(51) Int. Cl.⁷ .............................................. G01N 21/64
(52) U.S. Cl. .................................................. 250/461.2
(58) Field of Search .......................... 250/458.1, 459.1, 250/461.1, 461.2

(56) References Cited

U.S. PATENT DOCUMENTS 5,633,503 A * 5/1997 Kosaka ..................... 250/458.1

FOREIGN PATENT DOCUMENTS

| JP | 02281131 A | * | 11/1990 | ............ C12M 1/34 |
| JP | 05184579 A | * | 7/1993 | ............ A61B 5/00 |
| JP | 09023896 A | * | 1/1997 | ............ C12M 1/34 |
| JP | 10-323197 | | 12/1998 | ............ C12Q 1/02 |
| JP | 11178568 A | * | 7/1999 | ............ C12M 1/34 |
| WO | WO 9738128 A1 | * | 10/1997 | ............ C12Q 1/06 |

* cited by examiner

Primary Examiner—Constantine Hannaher
(74) Attorney, Agent, or Firm—Norris McLaughlin & Marcus PA

(57) ABSTRACT

A microorganism double-stained with appropriate fluorescent reagents is dropped onto a light permeable plate or passed through a micro-tube and irradiated with excitation light. As a result, the fluorescent reagents absorb the excitation light and thus the microorganism fluoresces. This fluorescence is detected by a CCD camera, a photodiode or a multiplier photo-tube and subjected to image-processing, thereby determining the amount and type of the microorganism and judging whether it has vital cells or dead cells.

6 Claims, 2 Drawing Sheets

METHOD AND APPARATUS FOR IMMEDIATELY DETERMINING MICROORGANISM

TECHNICAL FIELD OF THE INVENTION

The present invention relates to a method and an apparatus for immediately determining microorganisms; and particularly, relates to a method and an apparatus by which the amount and the type of a bacterium or a fungus can be measured and whether cells are vital or dead can be judged with an extremely high accuracy.

BACKGROUND OF THE INVENTION

In conventional methods to determine microorganisms, such as bacteria and fungii, the determination is carried out in such a manner that microorganisms are picked up from a specimen; the number of the microorganisms is appropriately adjusted and then cultivated for about 24 to 48 hours using an agar medium; the judgement of the microorganism is done with human eyes. In another method, it is known to vegetate microorganisms picked up from specimen on a culture, where chromo-enzyme has been mixed, and the microorganisms are cultivated for about 24~48 hours; the judgement of the microorganism is conducted using human eyes by dissolving the chromo-enzyme and developing the color with β-galactositase enzyme.

Further, the present inventor discloses a method for determining microorganism in Japanese Patent No. 2979383. The technique in this patent is that: a microorganism is double-stained with appropriate fluorescent reagents and the thus stained microorganism is processed so as to prevent that the fluorescent reagents flow out from the cells of the microorganism; then the thus processed microorganism is dropped onto a light permeable plate and an excited light is illuminated on the plate from underneath; the determination is carried out by human eye using a magnifying lens. According to this method, the microorganism is double-stained for obtaining different fluorescence from vital cells and dead cells, it is therefore possible to determine if the subjected microorganism is vital or dead. Furthermore, it is possible to judge the type and the number of the microorganism by measuring the dimension and counting the quantity of the fluorescents.

However, in a case where it is required to determine a microorganism immediately, the conventional method using a culture is not practical because it is required to cultivate microorganism for a long time. The other demerits are that: the types of microorganisms which are available to be determined are limited to only a few, such as *Escherichia coli* or general vital microorganisms, and it is difficult to judge if the microorganism is vital or dead. On the other hand, the method disclosed in the patent owned by the present applicant is to determine the stained microorganism with the aid of fluorescent reagents by human eyes using a magnifying lens. Accordingly, it has been desired to determine microorganisms more precisely.

The present invention has been carried out to solve the above-mentioned tasks and has for its purpose to provide a method and an apparatus for immediately determining microorganisms, where the amount or the type of bacterium or fungus can be judged and the judgement if the microorganism is vital or dead can be done with an extremely high accuracy and in a very short time period.

DISCLOSURE OF THE INVENTION

In order to solve the task mentioned above, the method for immediately determining microorganisms according to the present invention is characterized in that: a double-stained microorganism with appropriate fluorescent reagents is dropped onto a light permeable plate, which is processed to scatter light; an excitation light having a center wavelength of 488 nm is illuminated on the microorganism to the light permeable plate from underneath to make the microorganism fluoresce; an image of the microorganism which is fluorescing in this manner is picked up from the upper side with an image pick up means and then processed; and the amount or the type of microorganism and whether it is vital or dead are judged.

By illuminating an excitation light to the microorganisms, that have been double-stained with fluorescent reagents, the microorganism absorbs the excitation light and emits a strong fluorescence. It is not necessary to cultivate the stained microorganism, so that judgement can be done in a short time period. Furthermore, judgement can be carried out with a high accuracy by picking up an image of the microorganism emitting a fluorescence and processing the image, in comparison to judgement by human eyes; moreover, it is possible to correctly judge vital cells which are always floating. It should be noted that the double-stain of the microorganism should be conducted so that the vital cells and the dead cells emit different fluorescence, respectively.

The method for immediately determining microorganisms according to the invention has another aspect in that the microorganisms double-stained with appropriate fluorescent reagents are passed through a micro-tube having a light permeability; an excitation light having a center wavelength of 488 nm is illuminated on the microorganism passing through the micro-tube to make the microorganism fluoresce; the fluorescence of the microorganism is detected with the aid of a photo diode where an image of the fluorescence is converted into an electric signal; so that the amount, and the type of microorganism can be determined and it can be judged whether the cells are vital or dead. It should be noted that the photo-diode to detect fluorescence of the microorganism can be substituted by a multiplier photo-tube.

In such a construction, the double-stained microorganisms with fluorescent reagents pass through the micro-tube little by little. Therefore, when an excitation light is illuminated on the microorganism passing through the micro-tube, the determination of microorganism can be carried out one by one. In addition, since vital cells are always floating, they are generally difficult to determine. However, according to the invention, such a determination can be carried out with a high accuracy because it is conducted during when the microorganism is passing through the micro-tube.

Furthermore, according to the method for immediately determining the microorganism of the present invention, a microorganism to be determined is separated into two groups; one group is double-stained with appropriate reagents, while the other group is subjected to an antigen-antibody reaction in order to react specific bacteria contained in the group; the second group of microorganisms is double-stained with appropriate reagents after the antigen-antibody reaction. Then the judgement results of these two groups are compared to determine the amount of the specific bacteria and whether the bacteria are vital or dead.

By subjecting one of the groups of microorganisms to an antigen-antibody reaction before staining, causes the specific microorganisms to be covered with an antibody. In such a case, a specific microorganism does not fluoresce but another microorganism does. On the other hand, in the group which is not subjected to the antigen-antibody reaction, all of the microorganisms fluoresce; a normal determination is carried out. Therefore, by comparing the results of the judgements of these groups, the quantity of microorganisms, which are subjected to an antigen-antibody reaction, and where the microorganisms are vital or dead can be appropriately judged.

Moreover, the apparatus for immediately determining microorganism according to the invention, wherein an excitation light is illuminated on a microorganism double-stained with appropriate reagents to judge the quantity and the type of the microorganism and whether the microorganism is vital or dead, is characterized in that: the apparatus comprises a light source which emits an excitation light having a central wavelength of 488 nm, a light permeable plate processed so as to scatter a light, onto which a microorganism is dropped, an image picking up means for picking up an image of fluorescence on the light permeable plate, which is provided at a position opposite to said light source with respect to said light permeable plate, wherein the light source, the light permeable plate, said image picking up means are provided in a casing, inside of which is kept in a dark room condition.

Further, the apparatus for immediately determining microorganisms according to the invention wherein an excitation light is illuminated on a microorganism double-stained with appropriate reagents so as to judge the amount and the type of microorganism, and whether the microorganism is vital or dead, is characterized in that: the apparatus comprises a light source which emits an excitation light having a central wavelength of 488 nm, a micro-tube having a permeability through which said microorganism passes, a photo diode for detecting the microorganism which is passing through said micro-tube, which is provided at a position orthogonal to a light emitting axis of said light source with respect to said micro-tube, wherein said light source, said micro-tube, and said photo diode are provided in a casing, inside of which is kept in a dark room condition. It should be noted that the photo diode for detecting microorganism may be substituted by a multiplier photo-tube.

The method and apparatus according to the present invention has another aspect in that said image pick up means is a CCD camera.

The method and apparatus according to the preset invention has still another aspect in that the diameter of said micro-tube is in a range of 1 $\mu$m~10 $\mu$m. Taking the dimension of a microorganism into consideration, the microorganism can pass through the micro-tube little by little. It is preferred to determine the diameter of the micro-tube in accordance with the dimension of the microorganism to be determined in the range of 1 $\mu$m to 10 $\mu$m.

Moreover, the method and apparatus according to the present invention has still another aspect in that the apparatus further comprises a band pass filter means, which passes a light having a specific wavelength, and is provided, so that only the fluorescence from vital cells or dead cells can be extracted. By providing a band pass filter means, a fluorescence light having a specific wavelength can be detected from the microorganism, therefore it becomes possible to judge independently whether the microorganism is vital or dead.

BEST MODE OF THE INVENTION

Figure 1:
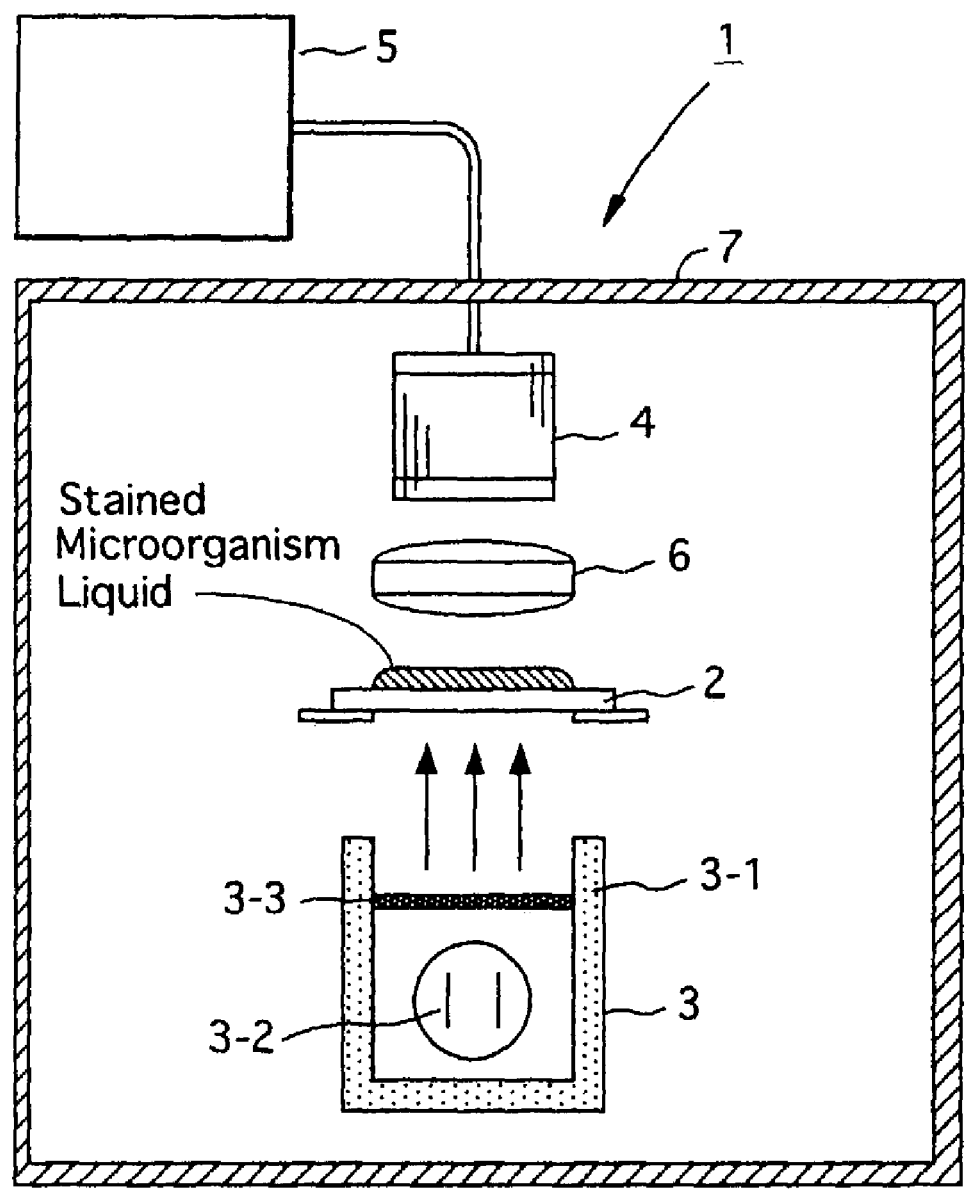
FIG. 1 is a schematic view showing a construction of the determining apparatus according to the first embodiment of the present invention.

The detail of the present invention will be explained below, referring to the attached drawings. FIG. 1 is a schematic view showing a construction of the determining apparatus according to the first embodiment. As shown in FIG. 1, the determining apparatus 1 comprises a light permeable plate 2 onto which a stained microorganism is dropped, an excitation light source 3 which illuminates an excitation light having a center wavelength of 488 nm (±10 nm) to the light permeable plate 2 from underneath, a CCD camera 4 provided opposite to the excitation light source 3 with respect to the light permeable plate 2; an image processor 5 where an image picked up by the CCD camera 4 is processed; and a magnifying lens 6 for magnifying microorganisms on the light permeable plate 2. The elements other than the image processor 5 are provided in a casing 7, inside of which is kept in a dark room condition.

The plate 2 is made of a light permeable material such as glass and acrylic resin; the plate 2 is processed so as to scatter light. A ground glass having a light scattering degree of 5 to 50 times is, for example, preferably used for the plate.

The excitation light source unit 3 has a construction such that a white pulse light source 3-2 is provided in an electromagnetic wave shielded tube 3-1, having an opening at one of the ends thereof. The excitation light source unit 3 illuminates an excitation light having a central wavelength of 488 nm, due to the applicability of the fluorescent reagents. The vital cells and dead cells fluorescent with different specific wavelengths, respectively. Therefore, the excitation light source unit 3 comprises a band pass filter 3—3 through which passes the light having a specific central wavelength of 488 nm in accordance with Stokes' law. A xenon lamp having an extreme high light intensity can be used for the white pulse light source 3-2. However, in such a xenon lamp, the stability of light amount is not high; therefore a plurality of LEDs (light emitting diodes) can be used instead. LEDs do not have a high intensity, but the stability is good. It should be noted that the specific wavelength which passes through the filter can appropriately be changed depending upon the fluorescent reagents to be used. Further, a conductive glass filter may be provided at the opening side of the electro-magnetic wave shielded tube 3-1 in order for conductivity to remove electric noise which is generated from the white pulse light emission. The desired light intensity and wavelength could be obtained by providing the conductive glass filter.

The CCD camera 4 picks up an image, which has been magnified with the magnifying lens 6; the image can be analyzed in the image processor 5. The image processor 5 has necessary equipment for processing the image picked up by the CCD camera 4, and a display (not shown) on which the image can be shown. The magnifying lens 6 having a magnification of ×200 or more is preferably used for the magnifying the image. The magnification can be appropriately changed depending on the size of the light permeable plate 2 or the type of the microorganism to be detected. The casing 7 is made of a material which can interrupt a light from the outside and has a good durability; for instance, steel plate or aluminum plate can be preferably used.

Next, the microorganism, i.e. the stained microorganism liquid, will be explained. The microorganism, for instance, bacteria or fungii, are appropriately obtained from the specimen. The microorganism can be obtained from a specimen in such a manner that a sterilization swab which contains balanced saline solution is put in on the specimen to adhere the microorganism, or a soluble cultivate is brought in contact with the surface of the specimen to adhere to the microorganism. The thus obtained microorganism is mixed in a stained liquid, which contains appropriate fluorescent reagents and stain accelerating agents with balanced saline solution.

Such fluorescent reagents can be used for staining microorganism that emit a strong fluorescent light having a central wavelength of 520 nm (±10 nm) when the reagents absorb an excitation light having a central wavelength of 488 nm (±10 nm). For instance, fluoresceindiacetate (FDA, $C_{24}H_{16}O_7$), acetoxymethyl-esterified Calcein(Calcein-AM, $C_{46}H_{46}N_2O_{23}$), CFSE($C_{29}H_{19}NO_{11}$), acetoxymethyl-esterified biscarboxyethylcarboxyfluorescein (BCECF-AM), carboxyfluorescein (CF, $C_{21}H_{12}O_7$) can be preferably used. These fluorescent reagents have characteristics in that the reagents permeate and disperse in vital cells of the microorganism, but when the reagents permeate in dead cells, the reagents are taken into the cells. Therefore, only vital cells emit a strong fluorescent light having a central wavelength of 520 nm when the reagents absorb the excited light.

On the other hand, such reagents are used that emit a strong fluorescent light having a central wavelength of 615 nm (±10 nm) when the reagents absorb an excitation light having a central wavelength of 488 nm (±10 nm). For instance, propidiumiodide (PI, $C_{27}H_{34}N_4I_2$), etc. can be preferably used. This fluorescent reagent cannot permeate into vital cells due to the existence of esterase in vital microorganism, however, it can permeate into dead cells and disperse therein. Therefore, when the reagent is given to the stained microorganism liquid, the reagent permeated in the dead cells emits a strong fluorescent light having a central wavelength of 615 nm (±10 nm). As stated above, in the present invention, microorganisms are stained in a doubled manner using two different fluorescent reagents, which allows one to judge whether the microorganism is vital or dead.

It is preferred that the above-mentioned fluorescent reagents have a concentration of at least 3 $\mu$mol/ml or more with respect to balanced saline solution in order that the reagents fluoresces when it absorbs an excitation light. While, since an exceeded concentration may badly influence vital cells, it is necessary to limit the concentration to at most 15 $\mu$mol/ml or less. On the other hand, the staining acceleration agent is used for making the permeation of the fluorescent reagents into the cells of the microorganism higher. The factor to inhibit the permeation of the reagents is the cell membrane of the microorganism. The staining acceleration agent has a function to soften the cell membrane; it is preferred that the agent has a concentration in a range of about 1 $\mu$mol/ml to 10 $\mu$mol/ml with respect to balanced saline solution. As the staining acceleration agent, for instance, salts (sodium chloride, magnesium chloride), kinetis or cellulase can be preferably used.

Next, the stained microorganism liquid obtained by the above-mentioned process is heated to a temperature of about 25~35° C. By this heating, the fluorescent reagents preferably permeate into the cells of the microorganism in conjunction with the function of the staining accelerator agent. In this case, the time for staining varies depending on the heating condition; it normally takes about 5~10 minutes.

As stated above, since the stain accelerator reagent is contained in the stained microorganism liquid, the cell membrane of the microorganism becomes soft. In this condition, there is a possibility that the fluorescent reagents may flow out from the cells once after the reagents permeate into the cells, so that the microorganism could not emit fluorescent light clearly. Therefore, it is preferred to use an agent for preventing the flow out, such as diethylstilbestrol or N, N' -dicyclohexylcarbodiimide. The concentration of the flow inhibiting agent is preferably about 5 $\mu$mol/ml to 20 $\mu$mol/ml with respect to balanced saline solution.

The method to determine a microorganism contained in the stained microorganism liquid will be explained. First, the liquid is dropped on the light permeable plate 2, and an excited light having a central wavelength of 488 nm (±10 nm) is illuminated from underneath of the plate. Then the fluorescent reagents mixed in the liquid, permeate into the cells of the microorganism, absorb the fluorescent light from underneath to fluoresce. As stated above, since the microorganisms are double-stained with two different types of fluorescent reagents, a strong fluorescent light having a central wavelength of 520 nm (±10 nm), which is green-yellow, is emitted from vital microorganisms, and a strong fluorescent light having a central wavelength of 615 nm (±10 nm), which is red-orange, is emitted from dead microorganisms, according to the Stokes' law.

The fluorescence has different sizes and is scattered and enlarged in a range of several times to several multiple times. Further, since the emission is magnified by the magnifying lens 6, the microorganism can be determined more clearly. According to the invention, the image magnified with the lens 6 is picked up by the CCD camera 4, then processed to determine the amount, types, whether the microorganism is vital or dead. Concretely, whether vital cells or dead cells is judged by the difference of color of the fluorescent light, the type of microorganism is determined by the shape and dimension of the emission, and the amount of the microorganism is counted by the number of the fluorescent emissions.

In the present embodiment, the image of microorganism dropped on the light permeable plate 2 is magnified with the magnifying lens 6 and picked up by the CCD camera 4. However, the magnifying lens 6 is able to magnify only one point on the light permeable plate 2, so that the area on the plate 2 as a whole cannot be enlarged at once. Therefore, it is arranged that the magnifying lens 6 and the CCD camera 4 are joined together so as to move them with a high speed keeping a parallel condition with respect to the light permeable plate 2, so that an image of the light permeable plate 2 as a whole can be picked up. Concretely, the area on the light permeable plate 2 is divided into plural regions, the CCD camera 4 is moved and stopped at each region to pick up an image of each and then the picked up images are sent to the image processor. In this manner, all microorganisms dropped on the light permeable plate 2 can be determined.

In order to judge whether the cells are vital or dead more efficiently in the present embodiment, it may be possible to provide a band pass filter through which a fluorescent emission light having a specific wave length can pass. For instance, in order to detect only vital microorganisms, a band pass filter, which permeates only fluorescent light having a central wavelength of 520 nm (±10 nm), may be provided between the light permeable plate 2 and the CCD camera 4.

In order to detect only dead microorganisms, a band pass filter which permeates only fluorescent light having a central wavelength of 615 nm (±10 nm) may be provided.

As explained above, according to the apparatus of the present embodiment, the color of the light emitted from the microorganism is different from vital microorganisms and dead microorganisms when illuminating the excitation light to the double-stained microorganisms. The determination can be carried out with high accuracy by picking up the fluorescence with the CCD camera and sending the image to the image processor. According to the invention, an accurate determination can be done for vital microorganisms which are always floating. Furthermore, by using a band pass filter which permeates only light having a specific wavelength, the fluorescence from vital cells or dead cells can be judged independently.

Figure 2A:
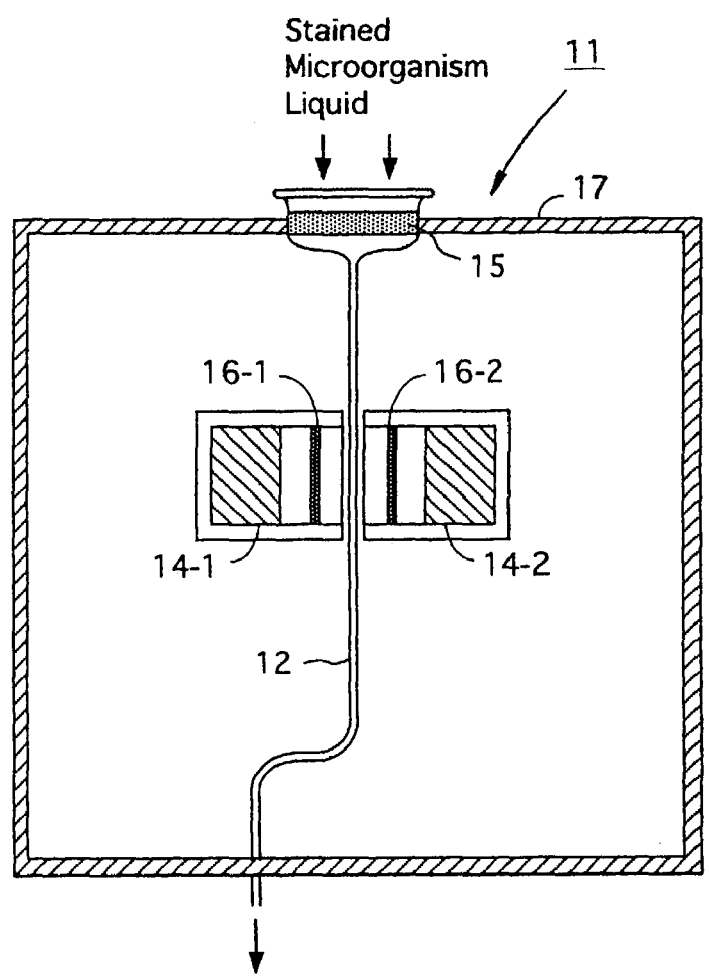
FIG. 2 is a schematic view illustrating a construction of the determining apparatus according to the second embodiment of the present invention.
Figure 2B:
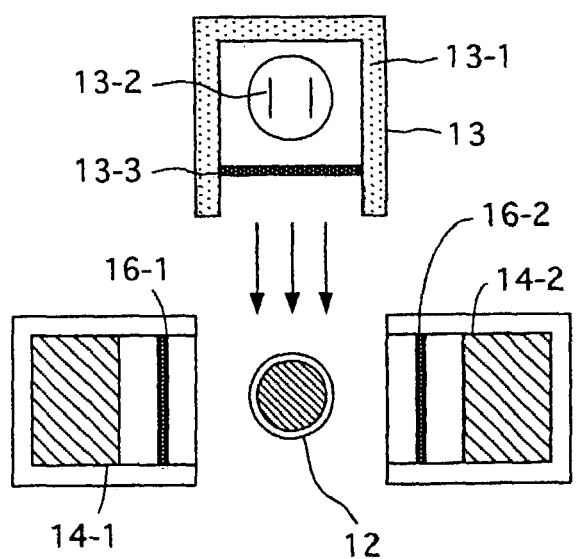

FIG. 2(a) is a schematic view showing a determining apparatus according to the second embodiment of the present invention; FIG. 2 (b) is a schematic view of the apparatus viewed from the upper side. As mentioned in FIG. 2, the determining apparatus 11 comprises a micro-tube 12 through which a stained microorganism passes, an excitation light source 13 (see FIG. 2(b)) which illuminates an excitation light having a central wavelength of 488 nm (±10 nm) to the micro-tube 12 from one side, and photo diodes 14 for converting the fluorescence from the microorganism to an electric signal. It should be noted that all of them are contained in the casing 17.

The micro-tube 12 has a diameter of the dimension of the microorganism to be measured, i.e. in a range of 1 μm to 10 μm, through which microorganisms can pass one by one. The diameter of the tube may be changed in accordance with the dimension of the microorganism to be measured. The tube 12 is composed of a material having a light permeability, for instance, glass or acrylic resin. At an inlet of the tube 12, a filter 15 is preferably provided for removing fine dust falling from the stained microorganism liquid, so that a highly accurate determination is available. It should be noted that the construction of the exited light source 13 and the casing 17 are the same as those explained in the first embodiment; the explanation therefor is omitted here.

The photo diodes 14-1, 14-2 are provided for detecting images of fluorescent emission from the vital cells or dead cells in the stained microorganism liquid passing though the micro-tube 12 and for converting the image into an electronic signal. It is preferred that the diodes detect the image with a detecting level of pico W. It should be noted that the photo diodes 14 are provided in two directions which cross with the illumination axis of the light source 13, respectively. Further, the diodes 14 have band pass filters 16-1, 16-2, respectively, which pass only a fluorescent light having a specific wavelength. That is to say, for the photo diode 14-1, is provided the filter 16-1 which passes only a fluorescent light emitted from vital microorganisms (central wavelength of 520 nm (±10 nm)), while, for the photo diode 14-2, is provided the filter 16-2 which passes only a fluorescent light emitted from dead microorganisms (central wavelength of 615 nm (±10 nm)). Each photo diode 14 is connected to a CPU where the picked up images are electrically processed. The CPU is further connected to a display or a counter display tube (not shown) to show the processing result.

Next, the method for determining microorganisms according to the second embodiment will be explained. It should be noted that in the second embodiment the stained microorganisms prepared by mixing microorganism and stained liquid is in the same manner as that of the first embodiment. Therefore, the explanation about the stained microorganism liquid is omitted here.

First, the stained microorganism liquid is put into the micro-tube 12 through an inlet. At this stage unnecessary dust is removed by the filter 15. As shown in FIG. 2(b), an excitation light is emitted from the excited light source 13 to the stained microorganism liquid passing through the micro-tube 12. The excited light has a central wavelength of 488 nm (±10 nm). Then, the fluorescent reagent permeated into the cells of microorganisms in the liquid absorbs the excitation light; then the microorganisms emit a fluorescent light. As stated above, since the microorganisms are stained in a doubled manner with two different types of reagent, a green-yellow fluorescent light having a central wavelength of 520 nm (±10 nm) is generated from vital microorganisms and a red-orange fluorescent light having a central wavelength of 615 nm (±10 nm) from dead microorganisms.

The photodiode 14-1 detects only the fluorescent light emitted from the vital microorganism due to the band pass filter 16-1, and the photo diode 14-2 detects only the fluorescent light emitted from dead microorganism due the band pass filter 16-2. The thus detected images are converted into electric signals. In the CPU, an average value of the converted electric signal can be calculated; the image can be appropriately magnified; and the electric signals detected by each of the diodes 14 can be synthesized. In this manner, whether the microorganisms are vital or dead is judged by the electric signal images; the type of the microorganisms can be determined by the shape and dimension of the fluorescent light and the number of the microorganisms can be detected from the quantity of fluorescence.

It should be noted that many modifications can be considered for this embodiment. For instance, multiplier photo-tubes can be substituted with the photo diodes 14. In this case, any type of multiplier photo-tubes can be used so far as it detects the fluorescent light emitted from the microorganisms; the image obtained by the multiplier photo-tubes are converted into electric signals and processed as in the same manner mentioned above to determine the microorganisms.

Various types of microorganisms are contained in the microorganisms to be determined, and in some cases it is desired to determine a specific type of microorganism. In such a case, it is considered to subject the specific microorganism to be determined to an antigen-antibody reaction. For instance, by reacting *Eschirchia coli* contained in the microorganisms to be determined with an antigen corresponding to the *Eschirchia coli*, only the *Eschirchia coli* can be detected. More concretely, the microorganisms to be determined are separated into two groups before staining the microorganism in a double manner. Then, one of the groups is double-stained with appropriate fluorescent reagents as mentioned above and determine the microorganism using fluorescent light emission. While, for the other group, subjecting the specific microorganism contained in the microorganism liquid to an antigen-antibody reaction first, and then the microorganism as a whole is double-stained with an appropriate fluorescent reagents to determine the microorganisms with the fluorescent emission.

In this case, the antibody attaches to the specific microorganism while the antigen-antibody reaction. Therefore, even when the microorganism is double-stained, the microorganism to which the antibody attaches, does not fluoresce, or such a microorganism fluoresce with a deviated wavelength. That is to say, in case of determining microorganisms including microorganisms subjected to an antigen-antibody reaction, the result is different from the double-stained determination for a normal microorganism. Therefore, by subtracting the result of the judgement where the microorganism is double-stained after the specific microorganism thereof is subjected to an antigen-antibody reaction from the result that the microorganism is normally double stained, the judgement of the amount or whether the microorganism is vital or dead, can be independently carried out. for the specific microorganism which is subjected to the antigen-antibody reaction In this case, it is preferred that the two judgements are carried out at the same time using the apparatus explained in the above. It may be possible to use only one part and carry the judgement twice. The antigen for the reaction should be decided depending upon the type of the microorganism to be determined.

As stated above, according to the determining apparatus of the second embodiment, the micro-tube used through which the microorganism can pass little by little, it is possible to determine the nature of microorganisms passing through the tube one by one. Further, the fluorescent emission from the microorganisms is detected with photo-diodes, etc and the detected image is subjected to an image processing, so that the determination can be carried out with extreme high accuracy; even vital microorganism which are always floating can be accurately determined. Furthermore, the photo-diodes comprise band pass filters, respectively, which pass lights having a different specific wavelength, so that the fluorescent light emission from vital microorganisms and dead organisms can independently be detected.

POSSIBILITY OF INDUSTRIAL APPLICATION

As mentioned above, according to the method and apparatus of the present invention, microorganisms are double-stained with an appropriate fluorescent reagents and an exited light is illuminated to the microorganisms; fluorescent lights having a different specific wavelengths are emitted from vital microorganisms and from dead microorganisms; the fluorescent lights are picked up by a CCD camera; therefore the judgement of the microorganisms can be done with a high accuracy and in a short time. Further, by using a micro-tube which passes microorganisms little by lettle and detecting the image of the microorganisms with photo-diodes, etc., it is possible to detect the microorganisms one by one so that the determination can be realized with a high accuracy. Furthermore, by the thus obtained images of the microorganism when subjected to an image processing, even vital microorganisms, which are always floating, can be detected precisely. Moreover, by subjecting microorganisms to an antigen-antibody reaction, a specific microorganism can be detected.

What is claimed is:

1. A method for immediately determining microorganisms, comprising the steps of:
   double-staining a sample of a selected microorganisms with appropriate fluorescent reagents, said sample comprising a plurality microorganism bodies
   selecting a micro-tube having a light permeability, wherein an internal diameter of the micro-tube is chosen to correspond to a diameter of the selected microorganism such that the microorganism bodies must pass through in single file at a particular location along the length thereof;
   passing the sample through the micro-tube,
   illuminating an excited light having a central wavelength of 488 nm through said micro-tube, whereby-the microorganism bodies emit flourescent light at a known wavelength,
   detecting the fluorescence of the microorganism bodies at said particular location by photodiodes or a multiplier photo-tube;
   converting the image of the detected fluorescence into electric signals; and
   determining from said electrical signals one or more of the amount of the microorganism bodies, a type of the microorganisms, and whether the microorganism bodies are vital or dead.

2. A method for immediately determining microorganisms according to claim 1, wherein said micro-tube has a diameter of about 1 $\mu$m–10 $\mu$m.

3. The method according to claim 1, wherein the fluorescence is selectively detected by providing a band pass filter which passes a light having a specific wavelength corresponding to either vital or dead micoorganism bodies.

4. The method according to claim 1, further comprising separating the microorganism sample into two groups;
   double staining a first group with appropriate fluorescent reagents,
   subjecting a second group to an antigen-antibody reaction so as to react a specific microorganism contained in the second group,
   double staining the first group and the second group with appropriate reagents; and
   comparing the data obtained from the determining step of of the first groups and the second group, whereby an amount of the specific microorganism and whether the specific microorganism is vital or dead may be determined.

5. An apparatus for immediately determining an amount and type of microorganisms which have been double stained with appropriate fluorescent reagents and whether the microorganisms are vital or dead the apparatus comprising a light source capable of emitting an excited light having a central wavelength of 488nm, a micro-tube having a light permeability, and an inside diameter of 1 $\mu$m–10 $\mu$m for permitting microorganism bodies to pass therethrough in single file; photo diodes or a multiplier photo-tube for detecting microorganism bodies passing through the micro-tube provided at a position opposite to said light source, and a casing surrounding said apparatus for maintaining a dark room condition.

6. An apparatus according to claim 5, further comprising a band pass filter which passes only a light having a specific wavelength corresponding to either vital or dead microorganism bodies.

* * * * *